United States Patent
Komatsu

(10) Patent No.: US 11,332,423 B2
(45) Date of Patent: May 17, 2022

(54) METHOD FOR PREPARING 1,2-DIFLUOROETHYLENE AND/OR 1,1,2-TRIFLUOROETHANE

(71) Applicant: DAIKIN INDUSTRIES, LTD., Osaka (JP)

(72) Inventor: Yuzo Komatsu, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 17/053,175

(22) PCT Filed: Apr. 25, 2019

(86) PCT No.: PCT/JP2019/017669
§ 371 (c)(1),
(2) Date: Nov. 5, 2020

(87) PCT Pub. No.: WO2019/216239
PCT Pub. Date: Nov. 14, 2019

(65) Prior Publication Data
US 2021/0163381 A1 Jun. 3, 2021

(30) Foreign Application Priority Data
May 7, 2018 (JP) .............................. JP2018-089063

(51) Int. Cl.
*C07C 17/20* (2006.01)
*B01J 23/26* (2006.01)
*C07C 17/25* (2006.01)
*C07C 19/08* (2006.01)
*C07C 21/18* (2006.01)

(52) U.S. Cl.
CPC .............. *C07C 17/20* (2013.01); *B01J 23/26* (2013.01); *C07C 17/25* (2013.01); *C07C 19/08* (2013.01); *C07C 21/18* (2013.01)

(58) Field of Classification Search
CPC ......... C07C 17/20; C07C 17/25; C07C 19/08; C07C 21/18; C07C 17/08; B01J 23/26
See application file for complete search history.

(56) References Cited

U.S. PATENT DOCUMENTS

| 3,432,562 A | * | 3/1969 | Gardner | ................. C07C 21/18 570/156 |
| 5,118,888 A | | 6/1992 | Gervasutti et al. | |
| 2007/0100172 A1 | * | 5/2007 | Mukhopadhyay | ..... B82Y 30/00 570/169 |
| 2016/0340565 A1 | | 11/2016 | Tasaka et al. | |

FOREIGN PATENT DOCUMENTS

| JP | 62-30730 | 2/1987 |
| JP | 2013-237624 | 11/2013 |
| JP | 2013-241348 | 12/2013 |
| JP | 2016-56132 | 4/2016 |
| WO | 2015/125874 | 8/2015 |
| WO | 2017/104828 | 6/2017 |

OTHER PUBLICATIONS

International Search Report dated Jul. 23, 2019 in International (PCT) Application No. PCT/JP2019/017669.
McBee et al., "Fluorinated Derivatives of Ethane", Indusuial and Engineering Chemistry, Mar. 1947, vol. 39, No. 3, pp. 409-412.
Ishikawa et al., "Fluorine Compounds—Their Chemistry and Applications", 1979, pp. 80-85, partial translation.
Sandler et al., "Organic Functional Group Preparations [I]", HIROKAWA-SHOTEN LTD., 1976. pp. 44-45, partial translation.
Nagai et al., KAGAKU KOGOYOSHA KK, Unit Process Series (3) Halogenation, Dehalogenation and Chlormethylation, 1964, pp. 38, 39, partial translation.
Extended European Search Report dated Jan. 27, 2022 in European Patent Application No. 19799257.1.

* cited by examiner

*Primary Examiner* — Jafar F Parsa
(74) *Attorney, Agent, or Firm* — Wenderoth, Lind & Ponack, L.L.P.

(57) ABSTRACT

This invention relates to a method for preparing 1,2-difluoroethylene and/or 1,1,2-trifluoroethane, comprising a step of performing at least one fluorination reaction by bringing at least one halide selected from the group consisting of haloethanes represented by general formula (1) $CHX^1X^2CH_2X^3$ (wherein $X^1$, $X^2$, and $X^3$ are the same or different, and represent Cl, Br, or F) and haloethylenes represented by general formula (2) $CHX^4=CHX^5$ (wherein $X^4$ and $X^5$ are the same or different, and represent Cl, Br or F, with the proviso that the case in which $X^4$ and $X^5$ are both F is excluded).

7 Claims, No Drawings

METHOD FOR PREPARING 1,2-DIFLUOROETHYLENE AND/OR 1,1,2-TRIFLUOROETHANE

TECHNICAL FIELD

The present disclosure relates to a method for preparing 1,2-difluoroethylene and/or 1,1,2-trifluoroethane.

BACKGROUND ART

In recent years, hydrofluoroolefins (HFO refrigerants) having a global warming potential (hereinafter simply referred to as GWP) lower than that of conventionally used HFC refrigerants have been attracting attention. Patent Literature 1 also studies 1,2-difluoroethylene (HFO-1132) as a refrigerant having a low GWP.

As a HFO-1132 preparation method, a method of obtaining HFO-1132 by subjecting 1,2-dichloro-1,2-difluoroethylene (CFO-1112) to a hydrodechlorination reaction in the presence of a hydrogenation catalyst is known, as disclosed in Patent Literature 2 and 3.

In addition, a method of obtaining HFO-1132 by a homocoupling reaction of $CH_2F_2$ and $CH_2ClF$, as disclosed in Patent Literature 4 and 5, is also known.

CITATION LIST

Patent Literature

PTL 1: WO2015/125874
PTL 2: JP1987-30730A
PTL 3: JP2016-56132A
PTL 4: JP2013-237624A
PTL 5: JP2013-241348A

SUMMARY OF INVENTION

Technical Problem

An object of the present disclosure is to provide a method for preparing HFO-1132 and/or HFC-143 with high conversion and selectivity.

Solution to Problem

The present inventors conducted extensive research to achieve the above object, and found that a method for preparing HFO-1132 and/or HFC-143 with high conversion and selectivity can be provided. The inventors conducted further research based on the above finding, and accomplished the present invention.

Specifically, the present disclosure provides the methods shown below for preparing HFO-1132 and/or HFC-143.

Item 1. A method for preparing 1,2-difluoroethylene and/or 1,1,2-trifluoroethane, comprising a step of performing at least one fluorination reaction by bringing at least one halide selected from the group consisting of haloethanes represented by general formula (1) $CHX^1X^2CH_2X^3$ (wherein $X^1$, $X^2$, and $X^3$ are the same or different, and represent Cl, Br, or F) and haloethylenes represented by general formula (2) $CHX^4=CHX^5$ (wherein $X^4$ and $X^5$ are the same or different, and represent Cl, Br, or F, with the proviso that the case in which $X^4$ and $X^5$ are both F is excluded) into contact with hydrogen fluoride.

Item 2. The preparation method according to Item 1, wherein the halide comprises at least one member selected from the group consisting of haloethanes represented by general formula (1-1) $CHX^1X^2CH_2X^3$ (wherein $X^1$, $X^2$, and $X^3$ are the same or different, and represent Cl or F) and haloethylenes represented by general formula (2-1) $CHX^4=CHX^5$ (wherein $X^4$ and $X^5$ are the same or different, and represent Cl or F, with the proviso that the case in which $X^4$ and $X^5$ are both F is excluded).

Item 3. The preparation method according to Item 1 or 2, wherein the halide comprises at least one member selected from the group consisting of 1,1,2-trichloroethane, 1-chloro-2,2-difluoroethane, and 1,2-dichloroethylene.

Item 4. The preparation method according to Item 1 or 2, comprising step A of performing a fluorination reaction by bringing 1-chloro-2,2-difluoroethane into contact with hydrogen fluoride to obtain 1,1,2-trifluoroethane.

Item 5. The preparation method according to Item 4, wherein the 1-chloro-2,2-difluoroethane in step A is obtained by step 1 of performing a fluorination reaction in which 1,1,2-trichloroethane and/or 1,2-dichloroethylene is/are brought into contact with hydrogen fluoride.

Item 6. The preparation method according to Item 5, comprising, in this order, step 1, step A, and step 2 of subjecting the 1,1,2-trifluoroethane to a dehydrofluorination reaction to obtain 1,2-difluoroethylene.

Item 7. The preparation method according to Item 5 or 6, wherein step 1 is performed in a gas phase in the presence of a catalyst.

Item 8. The preparation method according to Item 5 or 6, wherein step 1 is performed in a liquid phase in the presence of a catalyst.

Item 9. The preparation method according to any one of Items 4 to 6, wherein step A is performed in a gas phase.

Item 10. The preparation method according to any one of Items 4 to 6 and 9, wherein step A is performed in the presence of a chromium-based catalyst.

Advantageous Effects of Invention

According to the method for preparing HFO-1132 and/or HFC-143 of the present disclosure, a method for preparing HFO-1132 with high conversion and selectivity can be provided.

DESCRIPTION OF EMBODIMENTS

The preparation method of HFO-1132 or HFC-143 according to the present disclosure includes a step of performing at least one fluorination reaction by bringing at least one halide selected from the group consisting of haloethanes represented by general formula (1) $CHX^1X^2CH_2X^3$ (wherein $X^1$, $X^2$, and $X^3$ are the same or different, and represent Cl, Br, or F) and/or haloethylenes represented by general formula (2) $CHX^4=CHX^5$ (wherein $X^4$ and $X^5$ are the same or different, and represent Cl, Br, or F, with the proviso that the case in which $X^4$ and $X^5$ are both F is excluded) into contact with hydrogen fluoride. However, when the preparation method is a method for preparing HFC-143, it is preferable to exclude the case in which $X^1$, $X^2$, and $X^3$ in the above general formula (1) are all F.

According to the method for preparing HFO-1132 and/or HFC-143 of the present disclosure, a HFO-1132 preparation method in which the conversion is high and the selectivity of HFO-1132 in a reaction product is high can be provided. In particular, according to the preparation method of the present disclosure, 1,1,2-trifluoroethane (HFC-143), which is a precursor of HFO-1132, can be efficiently obtained.

Haloethane and Haloethylene

Olefins in this specification include both E-forms and Z-forms, unless otherwise specified.

The haloethanes used in the present disclosure are not limited, as long as they are represented by general formula (1) mentioned above; and known haloethanes can be widely used. Specific examples include 1,1,2-trichloroethane ($CHCl_2CH_2Cl$, hereinafter also simply referred to as HCC-140); 1,1-dichloro-1-fluoroethane ($CHFClCH_2Cl$, hereinafter also simply referred to as HCFC-141); 2-chloro-1,1-difluoroethane ($CHF_2CH_2Cl$, hereinafter also referred to simply as HCFC-142); 2-bromo-1,1-dichloroethane ($CHCl_2CH_2Br$, hereinafter also simply referred to as HCC-140B1); 1-bromo-1,2-dichloroethane ($CHClBrCH_2Cl$, hereinafter also simply referred to as HCC-140aB1); 1,1,2-tribromoethane ($CHBr_2CH_2Br$, hereinafter also simply referred to as HBC-140B3); 1,2-dibromo-1-fluoroethane ($CHFBrCH_2Br$, hereinafter, also simply referred to as HBFC-141B2); 2-bromo-1,1-difluoroethane ($CHF_2CH_2Br$, hereinafter, also simply referred to as HBFC-142B1); and the like. These can be used singly, or in a combination of two or more.

In the haloethane represented by general formula (1), it is preferable that $X^1$, $X^2$, and $X^3$ be the same or different, and represent Cl or F. $X^1$, $X^2$, and $X^3$ being Cl or F, rather than Br, ensures ease of availability; this is economically advantageous, and facilitates preparation on an industrial scale.

The haloethylene used in the present disclosure is not particularly limited, as long as it is represented by general formula (2); and known haloethylenes can be widely used. Specific examples include 1,2-dichloroethylene ($CHCl=CHCl$, hereinafter also simply referred to as HCO-1130); 1-chloro-2-fluoroethylene ($CHF=CHCl$, hereinafter also simply referred to as HCFO-1131); 1-bromo-2-chloroethylene ($CHBr=CHCl$, hereinafter also simply referred to as HBCO-1130B1); 1,2-dibromoethylene ($CHBr=CHBr$, hereinafter also simply referred to as HBO-1130); 1-bromo-2-fluoroethylene ($CHF=CHBr$, hereinafter also simply referred to as HBFO-1131); and the like. These can be used singly, or in a combination of two or more.

In the haloethylene represented by general formula (2), it is preferable that $X^4$ and $X^5$ be the same or different, and represent Cl or F (excluding the case in which both $X^4$ and $X^5$ are F). $X^4$ and $X^5$ being Cl or F, rather than Br, ensures ease of availability; this is economically advantageous, and facilitates preparation on an industrial scale.

That is, the halide preferably comprises at least one member selected from the group consisting of haloethanes represented by general formula (1-1) $CHX^1X^2CH_2X^3$ (wherein $X^1$, $X^2$, and $X^3$ are the same or different, and represent Cl or F), and haloethylenes represented by general formula (2-1) $CHX^4=CHX^5$ (wherein $X^4$ and $X^5$ are the same or different, and represent Cl or F, with the proviso that the case in which $X^4$ and $X^5$ are both F is excluded).

Of the haloethanes represented by general formula (1) and the haloethylenes represented by general formula (2), use of at least one member selected from the group consisting of HCC-140, HCFC-141, HCFC-142, HBFC-140B2, HBFC-142B1, HCO-1130, HCFO-1131, HBCO-1130B1, HBO-1130, and HBFO-1131 is particularly preferable because 1,2-difluoroethylene can be prepared with high selectivity. Considering the availability and economic efficiency of starting materials, HCC-140, HCFC-142, HCO-1130, and HCFO-1131 are more preferable.

Fluorination Reaction Step

The fluorination reaction with hydrogen fluoride may be a gas phase reaction or a liquid phase reaction. The number of fluorination reactions required to obtain HFO-1132 may be one or two or more, according to the halothane and haloethylene to be used.

In the case of a gas phase reaction, the starting material compound may be in a liquid state at the time of supply, as long as the starting material compound is in a gaseous state when brought into contact with hydrogen fluoride in the reaction temperature region mentioned below.

For example, if the starting material compound is liquid at normal temperature under normal pressure, halothane and/or haloethylene, which is the starting material compound, is evaporated with an evaporator and subsequently allowed to pass through a preheating region to be supplied to a mixing region where the halothane and/or haloethylene is/are brought into contact with hydrogen fluoride. This enables the reaction to be carried out in a gaseous state. The reaction may also be carried out by supplying the starting material compound in a liquid state to a reactor, and evaporating the starting material compound when the compound enters the reaction region where it reacts with hydrogen fluoride.

Further, as the hydrogen fluoride, it is preferable to use anhydrous hydrogen fluoride because corrosion of the reactor and deterioration of the catalyst can be suppressed.

There is no limitation to the method for evaporating the starting material compound in the reaction region, and known methods can be widely used. The starting material compound may be evaporated into a gaseous state by, for example, filling a reaction tube with a material that exhibits excellent thermal conductivity, exerts no catalytic activity in the fluorination reaction, and is stable with respect to hydrogen fluoride, such as nickel beads, Hastelloy pellets, or the like, so as to homogenize the temperature distribution within the reaction tube; heating the reaction tube to not less than the evaporation temperature of the starting material compound; and supplying the starting material compound in a liquid state.

There is no limitation to the method for supplying hydrogen fluoride to the reactor. For example, hydrogen fluoride is usually supplied to the reactor in a gaseous state with the starting material compound. The amount of the hydrogen fluoride supplied is preferably about 3 mol or more, more preferably about 3 to 100 mol, even more preferably about 5 to 100 mol, and still more preferably about 5 to 30 mol per mole of the starting material compound. By using such a composition, both the conversion of the starting material compound and the selectivity of the product such as HCFC-142 and HFC-143 can be maintained within a desirable range. In particular, by supplying 10 mol or more of hydrogen fluoride relative to 1 mol of the starting material compound, the selectivity of the product such as HCFC-142 or HFC-143 can be made extremely high.

In this specification, "conversion" means the ratio (mol %) of the total molar amount of compounds other than the starting material compound(s) contained in an outflow gas discharged from the outlet of the reactor relative to the molar amount of the starting material compound(s) supplied to the reactor.

In this specification, "selectivity" means the ratio (mol %) of the total molar amount of the target compound contained in an outflow gas discharged from the outlet of the reactor to the total molar amount of compounds other than the starting material compound(s) in the outflow gas.

The aforementioned starting material may be fed to the reactor as is; or may be diluted with an inert gas, such as nitrogen, helium, argon, or the like, and then fed to the reactor.

The type of a catalyst used for the fluorination reaction performed in the gas phase is not limited, and known catalysts used in the fluorination reaction of halogenated hydrocarbons can be widely used without limitation. Examples include oxides, hydroxides, halides, halogen oxides, and inorganic salts of chromium, aluminum, cobalt, manganese, nickel, or iron; and mixtures thereof. Of these, use of a chromium-based catalyst, such as $CrO_2$, $Cr_2O_3$, $FeCl_3/C$, $Cr_2O_3/Al_2O_3$, $Cr_2O_3/AlF_3$, $Cr_2O_3/C$, or $CoCl_2/Cr_2O_3$ in order to improve the conversion of the starting material is preferable. As chromium oxide/aluminum oxide catalysts, those described in U.S. Pat. No. 5,155,082, i.e., chromium oxide/aluminum oxide catalysts, and composites of halides of cobalt, nickel, manganese, rhodium, and ruthenium with the chromium oxide/aluminum oxide catalysts can be preferably used. Trichromium oxides, such as amorphous chromium oxide, are preferred. Of these, amorphous chromium oxide is most preferred. Chromium oxides having various particle sizes are commercially available. Additionally, the particle size and crystalline properties can be adjusted by precipitating chromium hydroxide from chromium nitrate and ammonia, followed by calcination. A fluorination catalyst having a purity of at least 98% is preferred. The catalysts selected from the above may be used singly, or in a combination of two or more There is no limitation to the form of the reactor used, and a known reactor can be widely used. For example, a tubular flow reactor packed with a catalyst may be used. When the reaction is conducted in the absence of a catalyst, a hollow adiabatic reactor, or an adiabatic reactor packed with a porous or nonporous metal or medium that improves the gas-phase mixing state between hydrogen fluoride and the starting material, can be used. In addition to this, it is preferable to use a multitubular reactor in which a heat medium is used to cool the reactor and homogenize the temperature distribution within the reactor.

When a hollow reactor is used, in a method wherein a reaction tube having a smaller inner diameter is used to improve heat transfer efficiency, it is preferable, for example, that the relationship between the flow rate of the starting material and the inner diameter of the reaction tube be adjusted so that a high linear velocity and a large heat transfer area can be obtained.

Regarding the reaction temperature at the time of gas-phase fluorination, the temperature in the reactor is preferably about 200 to 600° C., and more preferably about 230 to 430° C. By setting the reaction temperature to 200° C. or more, the selectivity of the target compound can be improved. Performing the reaction at a temperature of 600° C. or less may cause carbide to be produced and adhere to, or be deposited on, the reaction tube wall or filler, which reduces the risk of gradually clogging the reactor. However, when such a risk may exist, the carbide residue in the reaction tube may be removed by combustion by introducing oxygen into the reaction system together with the starting material compound; or by halting the reaction once, and allowing oxygen or air to pass through the reaction tube.

There is no limitation to the pressure during the reaction, as long as the aforementioned starting material compound and hydrogen fluoride can be present in a gaseous state. The reaction may be carried out under any pressure; i.e., normal pressure, increased pressure, or reduced pressure. Specifically, the preparation process may be conducted under reduced pressure or atmospheric pressure (0.1 MPa); and may also be conducted under increased pressure, so long as the starting material does not enter a liquid state.

There is no limitation to the reaction time. For example, the contact time represented by $W/F_0$, i.e., the ratio of the amount of packed catalyst $W(g)$ to the total flow rate $F_0$ (a flow rate at 0° C. and 0.1 MPa: cc/sec) of starting material gases supplied to the reaction system may be adjusted to a range of about 0.1 to 100 g·sec/cc, and preferably about 5 to 50 g·sec/cc. In this case, the total flow rate of starting material gas means the total flow rate of a chlorine-containing compound, which is the starting material, and a fluorinating agent; and, when used, inert gas, oxygen, etc.

On the other hand, when the fluorination reaction is performed in the liquid phase, known liquid phase fluorination catalysts can be widely used; and there is no limitation thereon. Specifically, at least one member selected from the group consisting of Lewis acids, transition metal halides, transition metal oxides, group IVb metal halides, and group Vb metal halides can be used.

More specifically, at least one member selected from the group consisting of antimony halide, tin halide, tantalum halide, titanium halide, niobium halide, molybdenum halide, iron halide, chromium fluoride halide, and chromium fluoride oxide can be used.

More specifically, catalysts, such as $SbCl_5$, $SbCl_3$, $SbF_5$, $SnCl_4$, $TaCl_5$, $TiCl_4$, $NbCl_5$, $MoCl_6$, and $FeCl_3$; and $SbCl_{(5-y)}F_y$, $SbCl_{(3-y)}F_y$, $SnCl_{(4-y)}F_y$, $TaCl_{(5-y)}F_y$, $TiCl_{(4-y)}F_y$, $NbCl_{(5-y)}F_y$, $MoCl_{(6-y)}F_y$, and $FeCl_{(3-y)}F_y$ (herein, the lower limit of y is 0.1 or more, and the upper limit of y is less than or equal to the valence of each element) adjusted by chloride salts and hydrogen fluoride are preferable. These catalysts may be used singly, or as a mixture of two or more. Of these, antimony pentachloride is particularly preferred.

When these catalysts become inactive, they can be easily regenerated by known techniques. As a method of regenerating a catalyst, a method of bringing chlorine into contact with the catalyst can be used. For example, about 0.15 to about 25 g/hr of chlorine per 100 g of a liquid phase fluorination catalyst can be added to the liquid phase reaction. The addition may be performed continuously at about 50 to 100° C. during the reaction.

For both the fluorination reaction in the gas phase and the fluorination reaction in the liquid phase, known reactors can be widely used, without limitation. It is preferable that the reactor be formed of a material, such as HASTELLOY, INCONEL, MONEL, or INCOLLOY, that is resistant to the corrosive action of hydrogen fluoride.

The preparation method of the present disclosure particularly preferably includes step A in which 1-chloro-2,2-difluoroethane (HCFC-142) is brought into contact with hydrogen fluoride to perform a fluorination reaction, thus obtaining 1,1,2-trifluoroethane (HFC-143). The presence of such step A increases the conversion and the selectivity of HFO-1132 in the reaction product under reaction conditions that are industrially easier than those in the prior art.

The HCFC-142 in step A is preferably obtained by step 1 in which 1,1,2-trichloroethane (HCC-140) and/or 1,2-dichloroethylene (HCO-1130) is/are brought into contact with hydrogen fluoride to perform a fluorination reaction. By employing such a preparation method, there is an advantage in that HFC-142 can be obtained with high selectivity from an easily available starting material, under reaction conditions in which industrially easy and continuous production is possible.

Dehydrofluorination Reaction Step

If necessary, a dehydrofluorination reaction may be carried out after the fluorination reaction. For example, HFC- 143, which is produced by the fluorination reaction, may be subjected to a dehydrofluorination reaction to obtain HFO-1132.

As the defluorination reaction method, known methods can be widely used without limitation. The defluorination reaction may be carried out in the liquid phase or the gas phase.

There is no limitation to the reaction temperature; or catalysts, if used. They can be appropriately determined.

In particular, when the HFC-1132 preparation method includes step 1 and step A, the preparation method preferably includes, in this order, step 1, step A, and step 2 in which the 1,1,2-trifluoroethane (HFC-143) obtained in step A is subjected to a dehydrofluorination reaction to obtain 1,2-difluoroethylene (HFO-1132). By using such a preparation method, there is an advantage in that HFC-1132 can be obtained with high selectivity under reaction conditions in which industrially easy and continuous production is possible.

Specific Embodiment 1

As described above, the HFO-1132 preparation method according to the present disclosure may include only one fluorination step; specifically, as described below, a method of subjecting haloethane represented by general formula (1) and/or haloethylene represented by general formula (2) to a fluorination reaction. In the chemical reaction formula below, HCC-140 and CHO-1130 are demonstrated as examples of haloethane and haloethylene, respectively; however, the present invention is not limited thereto. Alternatively, the fluorination reaction may be performed on a mixture of haloethane and haloethylene.

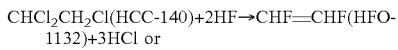
CHCl$_2$CH$_2$Cl(HCC-140)+2HF→CHF=CHF(HFO-1132)+3HCl or

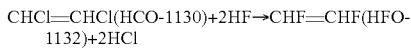
CHCl=CHCl(HCO-1130)+2HF→CHF=CHF(HFO-1132)+2HCl

Specific Embodiment 2

In the HFO-1132 preparation method according to the present disclosure, it is preferable that fluorination of haloethane represented by general formula (1) and/or haloethylene represented by general formula (2) be carried out to obtain HFO-143, and that HFO-143 is subjected to a dehydrofluorination reaction to obtain HFO-1132.

First Step

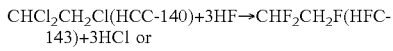
CHCl$_2$CH$_2$Cl(HCC-140)+3HF→CHF$_2$CH$_2$F(HFC-143)+3HCl or

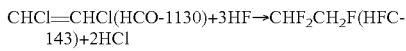
CHCl=CHCl(HCO-1130)+3HF→CHF$_2$CH$_2$F(HFC-143)+2HCl

Second Step

CHF$_2$CH$_2$F(HFC-143)→CHF=CHF(HFO-1132)+HF

Specific Embodiment 3

The HFO-1132 preparation method according to the present disclosure also includes an embodiment in which haloethane represented by general formula (1) and/or haloethylene represented by general formula (2) is/are subjected to the fluorination reaction two times or more. Specific examples include the following reaction.

First Step

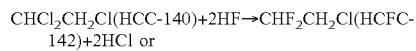
CHCl$_2$CH$_2$Cl(HCC-140)+2HF→CHF$_2$CH$_2$Cl(HCFC-142)+2HCl or

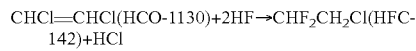
CHCl=CHCl(HCO-1130)+2HF→CHF$_2$CH$_2$Cl(HFC-142)+HCl

Second Step

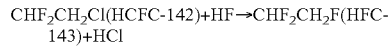
CHF$_2$CH$_2$Cl(HCFC-142)+HF→CHF$_2$CH$_2$F(HFC-143)+HCl

Third Step

CHF$_2$CH$_2$F(HFC-143)→CHF=CHF(HFO-1132)+HF

The embodiments according to the present invention are described as above. However, the present invention is not limited to such embodiments; and can include various embodiments, as long as they do not deviate from the gist of the invention.

EXAMPLES

Hereinbelow, the embodiments of the present invention are described in more detail below based on the Examples; however, the present invention is not limited thereto.

Preparation of HCFC-142 from HCC-140

A tubular Hastelloy reactor (inner diameter: 15 mm, length: 1 m) was packed with 10 g (fluorine content: about 15.0 mass %) of a catalyst obtained by subjecting chromium oxide represented by CrO$_2$ to a fluorination treatment, as a fluorination catalyst. The reactor was maintained at atmospheric pressure (0.1 MPaG) and at 250° C., and anhydrous hydrogen fluoride (HF) gas at a flow rate of 114 mL/min (flow rate at 0° C. and 0.1 MPa) was supplied to the reactor. The reactor was then maintained for 1 hour. Thereafter, CHCl$_2$CH$_2$Cl (HCC-140) was supplied at a flow rate of 5.6 mL/min (gas flow rate at 0° C., and 0.1 Mpa). The molar ratio of HF:HCC-140 was 20:1, and the contact time W/F$_0$ was 5.0 g·sec/cc. 4 hours after the start of the reaction, the conversion of HCC-140 was 20%, and the selectivity of CHF$_2$CH$_2$Cl (HCFC-142) was 92%.

Preparation of HCFC-142 from HCO-1130 (E)

A tubular Hastelloy reactor (inner diameter: 15 mm, length: 1 m) was packed with 10 g (fluorine content: about 15.0 mass %) of a catalyst obtained by subjecting chromium oxide represented by CrO$_2$ to a fluorination treatment as a fluorination catalyst. The reactor was maintained at atmospheric pressure (0.1 MPaG) and at 250° C., and anhydrous hydrogen fluoride (HF) gas at a flow rate of 114 mL/min (flow rate at 0° C. and 0.1 MPa) was supplied to the reactor. The reactor was then maintained for 1 hour. Thereafter, E-CHCl=CHCl (HCO-1130 (E)) was supplied at a flow rate of 5.6 mL/min (gas flow rate at 0° C., and 0.1 Mpa). The molar ratio of HF:HCO-1130 (E) was 20:1, and the contact time W/F$_0$ was 5.0 g·sec/cc. 4 hours after the start of the reaction, the conversion of HCO-1130 was 18%, and the selectivity of CHF$_2$CH$_2$Cl (HCFC-142) was 89%.

Preparation of HCFC-142 from HCFO-1131

A tubular Hastelloy reactor (inner diameter: 15 mm, length: 1 m) was packed with 10 g (fluorine content: about 15.0 mass %) of a catalyst obtained by subjecting chromium oxide represented by CrO$_2$ to a fluorination treatment, as a fluorination catalyst. The reactor was maintained at atmospheric pressure (0.1 MPaG) and at 250° C., and anhydrous hydrogen fluoride (HF) gas at a flow rate of 110 mL/min (flow rate at 0° C. and 0.1 MPa) was supplied to the reactor. The reactor was then maintained for 1 hour. Thereafter, CHF=CHCl (HCFO-1131) was supplied at a flow rate of 10.8 mL/min (gas flow rate at 0° C., and 0.1 Mpa). The molar ratio of HF:HCO-1131 was 10:1, and the contact time W/F$_0$ was 5.0 g·sec/cc. 4 hours after the start of the reaction, the conversion of HCFO-1131 was 21%, and the selectivity of $CHF_2CH_2Cl$ (HCFC-142) was 86%.

Preparation of HCFC-142 from HCC-140

As fluorination catalysts, $SbCl_5$ (30 g, 0.1 mol) and liquid hydrogen fluoride (200 mL, 10 mol) were introduced to a 500 mL-Hastelloy autoclave beforehand. The temperature in the reactor was set to 80° C. While maintaining the pressure in the system to 1.1 MpaG, $CHCl_2CH_2Cl$ (HCC-140) was supplied at 30 g/hr. The fluorination reaction proceeded while extracting gases from the outlet in the upper portion of the reactor. A fraction containing the reaction product (including unreacted HF and by-product HCl) was obtained from the outlet in the upper portion of the reactor. 93% of $CHF_2CH_2Cl$ (HCFC-142) was contained in the resulting organic matter.

Preparation of HCFC-142 from HCO-1130 (Z)

As fluorination catalysts, $SbCl_5$ (30 g, 0.1 mol) and liquid hydrogen fluoride (200 mL, 10 mol) were introduced to a 500 mL-Hastelloy autoclave beforehand. The temperature in the reactor was set to 80° C. While maintaining the pressure in the system to 1.1 MpaG, Z—CHCl=CHCl (HCO-1130 (Z)) was supplied at 30 g/hr. The fluorination reaction proceeded while extracting gases from the outlet in the upper portion of the reactor. A fraction containing the reaction product (including unreacted HF and by-product HCl) was obtained from the outlet in the upper portion of the reactor. 96% of $CHF_2CH_2Cl$ (HCFC-142) was contained in the resulting organic matter.

Preparation of HCFC-142 from HCFO-1131

As fluorination catalysts, $SbCl_5$ (30 g, 0.1 mol) and liquid hydrogen fluoride (200 mL, 10 mol) were introduced to a 500 mL-Hastelloy autoclave beforehand. The temperature in the reactor was set to 80° C. While maintaining the pressure in the system to 1.1 MpaG, CHF=CHCl (HCFO-1131) was supplied at 30 g/hr. The fluorination reaction proceeded while extracting gases from the outlet in the upper portion of the reactor. A fraction containing the reaction product (including unreacted HF and by-product HCl) was obtained from the outlet in the upper portion of the reactor. 96% of $CHF_2CH_2Cl$ (HCFC-142) was contained in the resulting organic matter.

Preparation of HFC-143 from HCFC-142

A tubular Hastelloy reactor (inner diameter: 25 mm, length: 1 m) was packed with 40 g (fluorine content: about 15.0 mass %) of a catalyst obtained by subjecting chromium oxide represented by composition formula: $CrO_2$ to a fluorination treatment, as a fluorination catalyst. The reactor was maintained at atmospheric pressure (0.1 MPa) and at 380° C., and anhydrous hydrogen fluoride (HF) gas at a flow rate of 114 mL/min (flow rate at 0° C. and 0.1 MPa) was supplied to the reactor. The reactor was then maintained for 1 hour. Thereafter, $CHF_2CH_2Cl$ (HCFC-142) was supplied at a flow rate of 5.6 mL/min (gas flow rate at 0° C., and 0.1 Mpa). The molar ratio of HF:HCFC-142 was 20:1, and the contact time W/F$_0$ was 20.0 g·sec/cc. 4 hours after the start of the reaction, the conversion of HCFC-142 was 70%, the selectivity of $CHF_2CH_2F$ (HFC-143) was 11%, and the selectivity of CHF=CHCl (HCFO-1131) was 86% (HCFO-1131 can be recycled as a starting material).

Preparation of HFC-143 from HBFC-142B1

A tubular Hastelloy reactor (inner diameter: 25 mm, length: 1 m) was packed with 40 g (fluorine content: about 15.0 mass %) of a catalyst obtained by subjecting chromium oxide represented by composition formula: $CrO_2$ to a fluorination treatment, as a fluorination catalyst. The reactor was maintained at atmospheric pressure (0.1 MPa) and at 380° C., and anhydrous hydrogen fluoride (HF) gas at a flow rate of 114 mL/min (flow rate at 0° C. and 0.1 MPa) was supplied to the reactor. The reactor was then maintained for 1 hour. Thereafter, $CHF_2CH_2Br$ (HBFC-142B1) was supplied at a flow rate of 5.6 mL/min (gas flow rate at 0° C., and 0.1 Mpa). The molar ratio of HF:HBFC-142B1 was 20:1, and the contact time W/F$_0$ was 20.0 g·sec/cc. 4 hours after the start of the reaction, the conversion of HBFC-142B1 was 78%, the selectivity of $CHF_2CH_2F$ (HFC-143) was 31%, and the selectivity of CHF=CHBr (HBFO-1131B1) was 64% (HBFO-1131B1 can be recycled as a starting material).

Preparation of HFO-1132 from HFC-143

A tubular Hastelloy reactor (inner diameter: 15 mm, length: 1 m) was packed with 10 g (fluorine content: about 15.0 mass %) of a catalyst obtained by subjecting chromium oxide represented by composition formula: $CrO_2$ to a fluorination treatment, as a fluorination catalyst. The reactor was maintained at atmospheric pressure (0.1 MPa) and at 400° C., and $CHF_2CH_2F$ (HFC-143) was supplied to the reactor at a flow rate of 15.0 mL/min (flow rate at 0° C. and 0.1 MPa). The contact time W/F$_0$ was 40.0 g·sec/cc. 4 hours after the start of the reaction, the conversion of HCFC-143 was 98%, and the selectivity of CHF=CHF (HFO-1132) was 89% (E/Z=19/81).

The invention claimed is:

1. A method for preparing 1,2-difluoroethylene and/or 1,1,2-trifluoroethane, comprising step A of performing a fluorination reaction by bringing 1-chloro-2,2-difluoroethane into contact with hydrogen fluoride to obtain 1,1,2-trifluoroethane.

2. The preparation method according to claim 1 comprising in this order, step 1 of performing a fluorination reaction in which 1,1,2-trichloroethane and/or 1,2-dichloroethylene is/are brought into contact with hydrogen fluoride to obtain 1-chloro-2,2-difluoroethane, and step A.

3. The preparation method according to claim 2, comprising, in this order, step 1, step A, and step 2 of subjecting the 1,1,2-trifluoroethane to a dehydrofluorination reaction to obtain 1,2-difluoroethylene.

4. The preparation method according to claim 2, wherein step 1 is performed in a gas phase in the presence of a catalyst.

5. The preparation method according to claim 2, wherein step 1 is performed in a liquid phase in the presence of a catalyst.

6. The preparation method according to claim 1, wherein step A is performed in a gas phase.

7. The preparation method according to claim 1, wherein step A is performed in the presence of a chromium-based catalyst.

\* \* \* \* \*